(12) United States Patent
El-Lateef Ahmed et al.

(10) Patent No.: US 11,932,619 B1
(45) Date of Patent: Mar. 19, 2024

(54) 3-(2-(6-METHOXYPYRIDIN-3-YL)-4,5-DIPHENYL-1H-IMIDAZOL-1-YL)-N,N-DIMETHYLPROPAN-1-AMINE AS AN ANTICANCER COMPOUND

(71) Applicant: KING FAISAL UNIVERSITY, Al-Ahsa (SA)

(72) Inventors: Hany Mohamed Abd El-Lateef Ahmed, Al-Ahsa (SA); Mai Mostafa Khalaf Ali, Al-Ahsa (SA); Antar Ahmed Abdelhamid Ahmed, Al-Baha (SA); Adel A. Marzouk, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/367,895

(22) Filed: Sep. 13, 2023

(51) Int. Cl.
*C07D 401/04* (2006.01)
*A61P 35/00* (2006.01)

(52) U.S. Cl.
CPC ............ *C07D 401/04* (2013.01); *A61P 35/00* (2018.01); *C07B 2200/13* (2013.01)

(58) Field of Classification Search
CPC ................................ C07D 401/04; A61P 35/00
See application file for complete search history.

(56) References Cited

U.S. PATENT DOCUMENTS 8,129,394 B2   3/2012   Hunag et al.

OTHER PUBLICATIONS

Aruchamy, et al., Imidazole-pyridine hybrids as potent anti-cancer agents, Eur. J. Pharm. Sci., 180 (2023) (Year: 2023).*
Laufer, Stefan A., et al. "Novel substituted pyridinyl imidazoles as potent anticytokine agents with low activity against hepatic cytochrome P450 enzymes." Journal of medicinal chemistry 46.15 (2003): 3230-3244.
Aruchamy, Baladhandapani, et al. "Imidazole-pyridine hybrids as potent anti-cancer agents." European Journal of Pharmaceutical Sciences 180 (2023): 106323.
4,4',4"-(1H-imidazole-2,4,5-triyl)tripyridine; printed on Jul. 18, 2023.
Sharma, Pankaj, et al. "Imidazoles as potential anticancer agents: An update on recent studies." Molecules 26.14 (2021): 4213.
Umar, Abdullahi Bello, et al. "Investigation of Novel Imidazole Analogues with Terminal Sulphonamides as Potential V600E-BRAF Inhibitors Through Computational Approaches." Chemistry Africa (2023): 1-12.
4-(2-(1-Fluoronaphthalen-2-yl)-5-(4-fluorophenyl)-1H-imidazol-4-yl)pyridine; printed on Jul. 18, 2023.

* cited by examiner

*Primary Examiner* — Erich A Leeser
(74) *Attorney, Agent, or Firm* — Nath, Goldberg & Meyer; Richard C. Litman

(57) ABSTRACT

A 3-(2-(6-Methoxypyridin-3-yl)-4,5-diphenyl-1H-imidazol-1-yl)-N,N-dimethylpropan-1-amine compound, its synthesis, and its use as an anticancer agent.

11 Claims, 3 Drawing Sheets

3-(2-(6-METHOXYPYRIDIN-3-YL)-4,5-DIPHENYL-1H-IMIDAZOL-1-YL)-N,N-DIMETHYLPROPAN-1-AMINE AS AN ANTICANCER COMPOUND

BACKGROUND

1. Field

The present disclosure relates to the compound 3-(2-(6-Methoxypyridin-3-yl)-4,5-diphenyl-1H-imidazol-1-yl)-N, N-dimethylpropan-1-amine, its synthesis, and its use as an antitumor.

2. Description Of The Related Art

There remains an ongoing need for new therapeutically active agents for treating a variety of diseases, disorders, and conditions including, but not limited to, various forms of cancer, and the like.

Further, once such new therapeutically active agents are designed and/or discovered, they are often difficult to synthesize and/or prepare. It remains difficult to prepare such compounds without using solvents, to obtain a high yield, based on efficient reaction times, which are easy to use, and which involve a catalyst that can be recycled.

Thus, new molecules having desired therapeutic activities and solving the aforementioned problems are desired.

SUMMARY

The present subject matter relates to a multisubstituted imidazole compound having a substituent at the N1-position. In addition, the present subject matter relates to derivatives with a potential electron-releasing pyridine derivative substituent at the carbon 2 atom. The product can be acquired in exceptional yields (average about 90%) using a four-component cyclocondensation reaction between diphenylethanedione, aliphatic amines (N,N-dimethyl-3-aminopropane) and 6-methoxy-3-pyridinecarboxaldehyde together with $CH_3COONH_4$. The reaction can employ an ionic liquid catalyst, piperidinium hydrogen sulfate (PHS), without using any solvents, making this a pure synthetic method. The important characteristics of using this method are excellent yielding products, limitation of the reaction times, and ease of use. Additionally, the reaction components could be purified by some non-chromatographic technique and the ionic liquid catalysts can be recycled again and used with this efficiency. The product can be analyzed using spectral data; IR, NMR & elemental analysis. The prepared compound can be used for anticancer activity, which gave high efficiency. In an embodiment, the present subject matter relates to a 3-(2-(6-methoxypyridin-3-yl)-4,5-diphenyl-1H-imidazol-1-yl)-N,N-dimethylpropan-1-amine compound having the formula I:

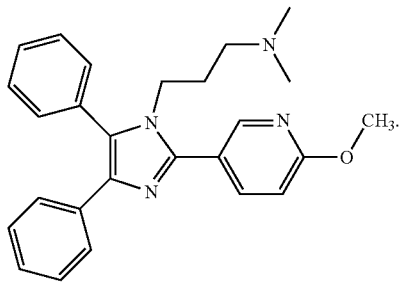

I

In another embodiment, the present subject matter relates to a pharmaceutically acceptable composition comprising a therapeutically effective amount of the 3-(2-(6-methoxypyridin-3-yl)-4,5-diphenyl-1H-imidazol-1-yl)-N,N-dimethylpropan-1-amine compound and a pharmaceutically acceptable carrier.

In a further embodiment, the present subject matter relates to a method of treating cancer in a patient comprising administering to a patient in need thereof a therapeutically effective amount of the 3-(2-(6-methoxypyridin-3-yl)-4,5-diphenyl-1H-imidazol-1-yl)-N,N-dimethylpropan-1-amine compound.

In one more embodiment, the present subject matter relates to a method of making the 3-(2-(6-methoxypyridin-3-yl)-4,5-diphenyl-1H-imidazol-1-yl)-N,N-dimethylpropan-1-amine compound, the method comprising: adding benzil, 6-methoxy-3-pyridinecarboxaldehyde, ammonium acetate, and N,N-dimethyl-3-aminopropane to piperidinium hydrogen sulfate in an oil bath to obtain a reaction mixture; heating the reaction mixture with stirring until reaction completion to obtain a crude product; purifying the crude product by recrystallization using absolute ethyl alcohol; and obtaining the 3-(2-(6-methoxypyridin-3-yl)-4,5-diphenyl-1H-imidazol-1-yl)-N,N-dimethylpropan-1-amine compound.

These and other features of the present subject matter will become readily apparent upon further review of the following specification.

DETAILED DESCRIPTION OF THE PREFERRED EMBODIMENTS

Figure 1:
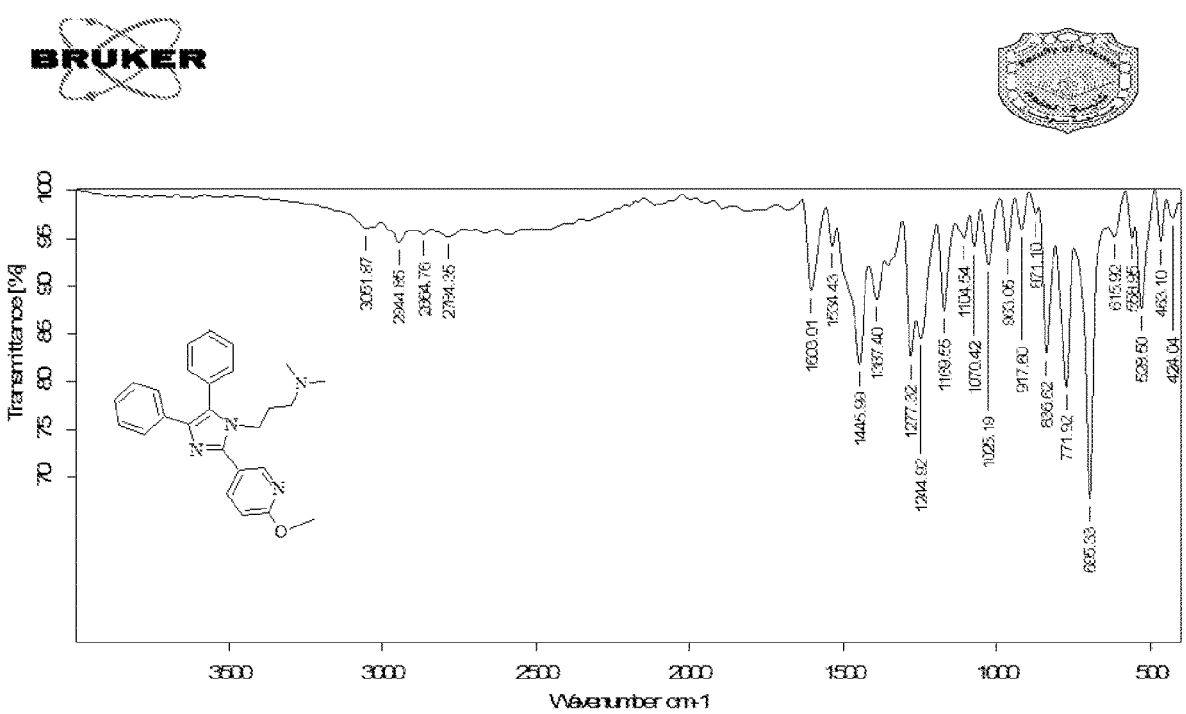
FIG. 1 shows an IR analysis of the 3-(2-(6-methoxypyridin-3-yl)-4,5-diphenyl-1H-imidazol-1-yl)-N,N-dimethylpropan-1-amine compound.

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as cancer.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The present subject matter relates to a multisubstituted imidazole compound having a substituent at the N1-position. In addition, the present subject matter relates to derivatives with a potential electron-releasing pyridine derivative substituent at the carbon 2 atom. The product can be acquired in exceptional yields (average about 90%) using a four-component cyclocondensation reaction between diphenylethanedione, aliphatic amines (N,N-dimethyl-3-aminopropane) and 6-methoxy-3-pyridinecarboxaldehyde together with $CH_3COONH_4$. The reaction can employ an ionic liquid catalyst, piperidinium hydrogen sulfate (PHS), without using any solvents, making this a pure synthetic method. The important characteristics of using this method are excellent yielding products, limitation of the reaction times, and ease of use.

Additionally, the reaction components could be purified by some non-chromatographic technique and the ionic liquid catalysts can be recycled again and used with this efficiency. The product can be analyzed using spectral data; IR, NMR & elemental analysis. The prepared compound can be used for anticancer activity, which gave high efficiency.

In an embodiment, the present subject matter relates to a 3-(2-(6-methoxypyridin-3-yl)-4,5-diphenyl-1H-imidazol-1-yl)-N,N-dimethylpropan-1-amine compound having the formula I:

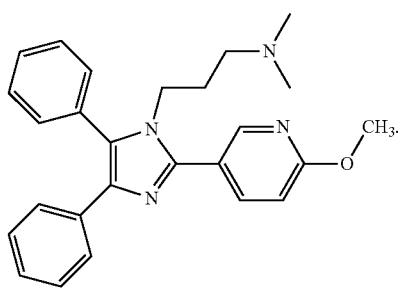

In certain embodiments, the 3-(2-(6-methoxypyridin-3-yl)-4,5-diphenyl-1H-imidazol-1-yl)-N,N-dimethylpropan-1-amine compound can be obtained as crystals. In further embodiments, the 3-(2-(6-methoxypyridin-3-yl)-4,5-diphenyl-1H-imidazol-1-yl)-N,N-dimethylpropan-1-amine compound can have a melting point of about 125° C. to about 127° C.

In another embodiment, the present subject matter relates to a pharmaceutically acceptable composition comprising a therapeutically effective amount of the 3-(2-(6-methoxypyridin-3-yl)-4,5-diphenyl-1H-imidazol-1-yl)-N,N-dimethylpropan-1-amine compound and a pharmaceutically acceptable carrier.

In this regard, the present subject matter is further directed to pharmaceutical compositions comprising a therapeutically effective amount of the compound as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises a present compound together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compound is typically administered at a therapeutically or pharmaceutically effective dosage, e.g., a dosage sufficient to provide treatment for cancer or a microbial infection. Administration of the compound or pharmaceutical compositions thereof can be by any method that delivers the compound systemically and/or locally. These methods include oral routes, parenteral routes, intraduodenal routes, and the like.

While human dosage levels have yet to be optimized for the present compound, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compound for treatment of cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present compound, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microtine powder for insufflation, alone or in combination with an inert carrier such as lactose. In such a case, the particles of the formulation have diameters of less than 50 microns, for example less than 10 microns.

In a further embodiment, the present subject matter relates to a method of treating cancer in a patient comprising administering to a patient in need thereof a therapeutically effective amount of the 3-(2-(6-methoxypyridin-3-yl)-4,5-diphenyl-1H-imidazol-1-yl)-N,N-dimethylpropan-1-amine compound.

In certain embodiments in this regard, the cancer can be one or more selected from the group consisting of leukemia, melanoma, colon cancer, prostate cancer, lung cancer, pancreatic cancer, osteosarcoma, and breast cancer. In an additional embodiment, the cancer can be prostate cancer or osteosarcoma.

In one more embodiment, the present subject matter relates to a method of making the 3-(2-(6-methoxypyridin-3-yl)-4,5-diphenyl-1H-imidazol-1-yl)-N,N-dimethylpropan-1-amine compound, the method comprising: adding benzil, 6-methoxy-3-pyridinecarboxaldehyde, ammonium acetate, and N,N-dimethyl-3-aminopropane to piperidinium hydrogen sulfate (ionic liquid) in an oil bath to obtain a reaction mixture; heating the reaction mixture with stirring until reaction completion to obtain a crude product; purifying the crude product by recrystallization using absolute ethyl alcohol; and obtaining the 3-(2-(6-methoxypyridin-3-yl)-4,5-diphenyl-1H-imidazol-1-yl)-N,N-dimethylpropan-1-amine compound.

The present production methods can be further seen by referring to the following Scheme 1:

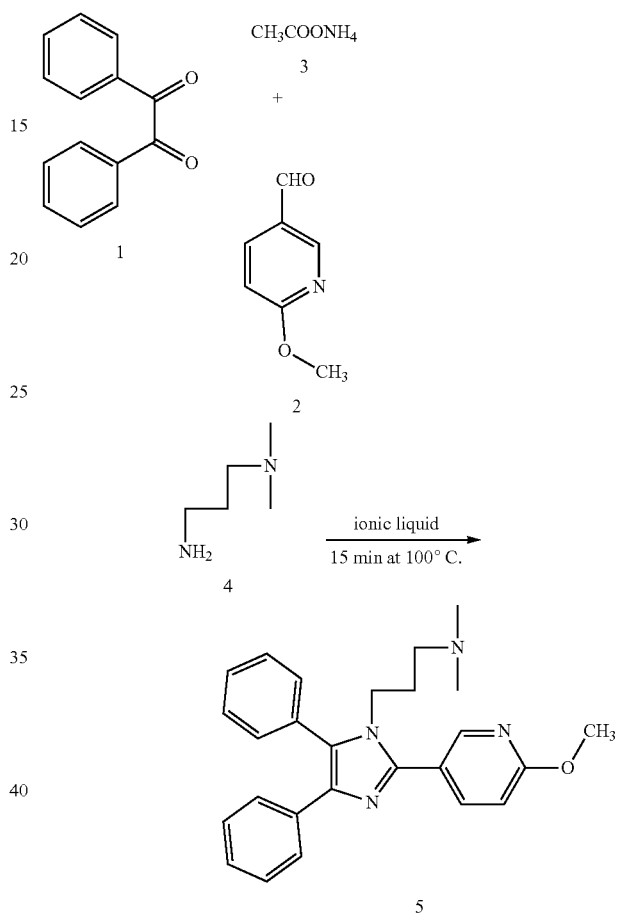

In an embodiment of the present production methods, the oil bath can be at a temperature of about 20° C. to about 30° C., or about 25° C.

In another embodiment of the present production methods, the heating can be at a temperature of about 100° C.

In a further embodiment of the present production methods, after reaction completion the reaction mixture can be washed with water.

In an embodiment of the present production methods, the benzil, 6-methoxy-3-pyridinecarboxaldehyde, and ammonium acetate can be added in an about 1:1:1 molar ratio. Similarly, the benzil, 6-methoxy-3-pyridinecarboxaldehyde, ammonium acetate, and N,N-dimethyl-3-aminopropane are added in an about 1:1:1:0.5 molar ratio.

In an additional embodiment of the present production methods, the 3-(2-(6-methoxypyridin-3-yl)-4,5-diphenyl-1H-imidazol-1-yl)-N,N-dimethylpropan-1-amine compound can be obtained in an about 87% yield.

In another embodiment, the catalytic piperidinium hydrogen sulfate (ionic liquid) can be recycled and reused in another process.

The following examples relate to various methods of manufacturing the specific compounds and application of the same, as described herein. All compound numbers expressed herein are with reference to the synthetic pathway figures shown above.

EXAMPLES

Example 1

Preparation of Catalytic Ionic Liquid (Piperidinium Hydrogen Sulfate (PHS))

Hexahydropyridine (200 mmole) was added to a three necked flask (150 ml) with a magnetic stirrer. An (20 mmol) equimolar quantity of $H_2SO_4$ (concentrated) was added sluggishly into the flask at an ice path. The mixture of the reaction was then stirred at 79° C. for 12 hrs, washed with ethoxyethane many times to isolate non-ionic deposits and dried in vacuum on a rotary evaporator to produce piperidinium hydrogen sulfate as a sticky liquefied compound.

Example 2

Preparation of 3-(2-(6-methoxypyridin-3-yl)-4,5-diphenyl-1H-imidazol-1-yl)-N,N-dimethylpropan-1-amine Benzil (20 mmole), 6-Methoxy-3-pyridinecarboxaldehyde (20 mmole), ammonium acetate (20 mmole) and N,N-dimethyl-3-aminopropane (10 mmol) were added to piperidinium hydrogen sulfate (8 mmole) in an oil bath at 25° C. The producing mixture was heated to 100° C. for the appropriate time. After the reaction was completion then checked using thin layer chromatography, the reaction mixture washed with $H_2O$, the yielded product purified through recrystallization from the absolute ethyl alcohol.

Figure 2:
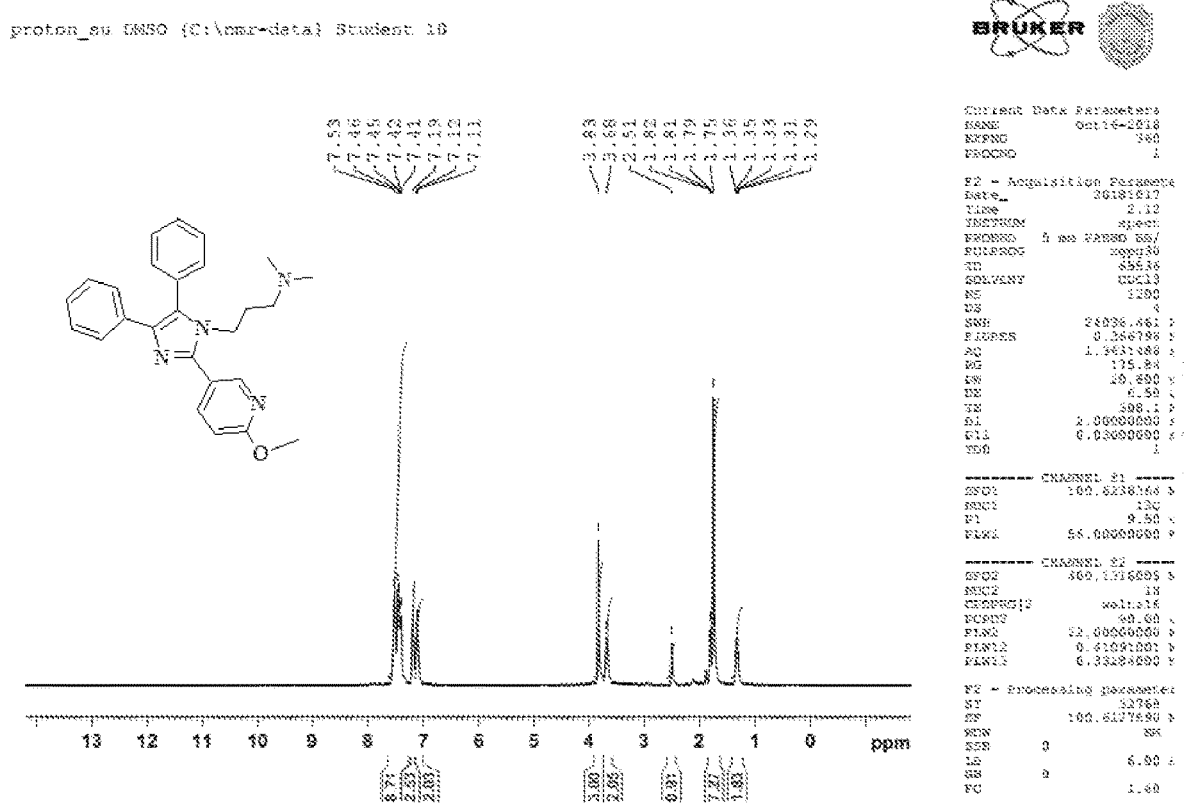
FIG. 2 shows a $^1H$ NMR analysis of the 3-(2-(6-methoxypyridin-3-yl)-4,5-diphenyl-1H-imidazol-1-yl)-N,N-dimethylpropan-1-amine compound.
Figure 3:
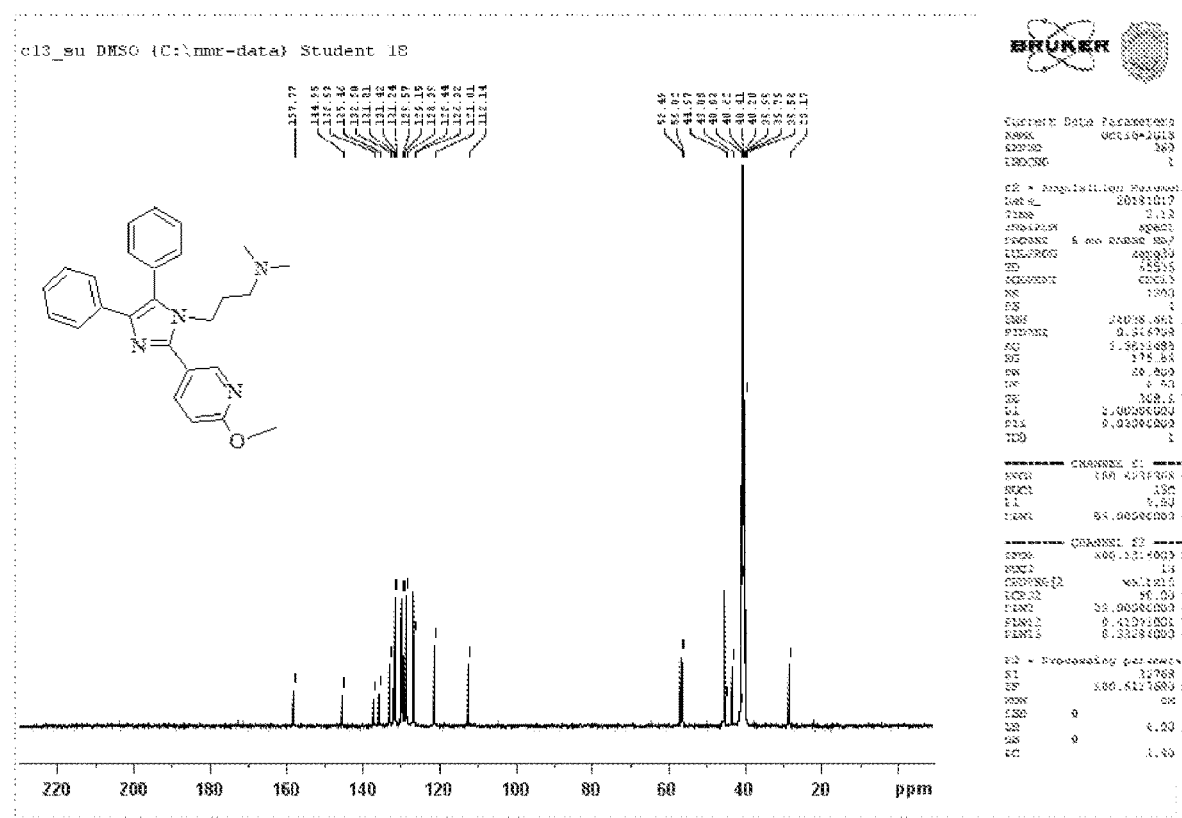
FIG. 3 shows a $^{13}C$ NMR analysis of the 3-(2-(6-methoxypyridin-3-yl)-4,5-diphenyl-1H-imidazol-1-yl)-N, N-dimethylpropan-1-amine compound.

Characterization of the prepared compound using IR, $^1H$ NMR, and $^{13}C$ NMR analysis is shown in FIGS. 1-3, respectively. The elemental analysis can be seen as follows.

3-(2-(6-Methoxypyridin-3-yl)-4,5-diphenyl-1H-imidazol-1-yl)-N,N-dimethylpropan-1-amine (5): Mp. 125-127° C. yield=87%, FTIR (KBr, cm$^{-1}$): 3052 (C—H), 2945-2785 (C—H), 1604 (N=C); $^1H$ HNMR (DMSO-d$_6$/D$_2$O, 400 MHz): 1.31 (m., 2H, N–H$_2$C–H$_2$C–H$_2$C-N), 1.75 (s., 6H, N(CH$_3$)$_2$), 1.81 (t., 2H, N–H$_2$C–H$_2$C–H$_2$C-N), 3.68 (t. 2H, N–H$_2$C—H$_2$C—H$_2$C—N)), 3.83 (s., 3H, OMe), 7.12-7.54 (m., 13H, Aryl-H), $^{13}C$—NMR (100 MHz, DMSO-d$_6$): 28.17, 43.08, 44.57, 56.02, 56.45, 112.14, 121.01, 126.22, 126.44, 128.35, 129.57, 131.24, 131.42, 131.81, 132.60, 135.46, 136.46, 144.55, 157.77. Analysis: calculated for C$_{26}$H$_{28}$N$_4$O (412.52): C, 75.70; H, 6.84; N, 13.58%. Found: C, 75.68; H, 6.81; N, 13.55%.

Example 3

Anti-Cancer Activity

Cell Lines and Culture Conditions

The human prostate cancer cells (PC3) and human osteosarcoma cells (MG-63) were obtained from Nawah Scientific Inc. (Mokatam, Cairo, Egypt) and cultured in DMEM (Dulbecco's modified eagle's medium), Gibco, USA, supplemented with fetal bovine serum (FBS) at a concentration of 10% and 100 U/mL of penicillin and streptomycin (PS). The Cells were incubated at 37° C. in a humidified environment that contained 5% $CO_2$.

Assessment of Cytotoxicity by SRB Assay

Cells were seeded in 96-well plates as aliquots of 100 μL cell suspension and incubated in a complete media for 24 h. afterward, cells were treated with 3-(2-(6-Methoxypyridin-3-yl)-4,5-diphenyl-1H-imidazol-1-yl)-N,N-dimethylpropan-1-amine at diverse concentrations ranging from 0.01 μM to 100 μM for 72 h. Then, cells were fixed at 4° C. for one hour with 150 μL of 10% trichloroacetic acid (TCA). After washing the cells five times with distilled water, 70 μL of sulforhodamine (SRB) solution (0.4% w/v) was added and incubated for 10 min at room temperature in a dark place. Cells were washed with 1% acetic acid three times and allowed to air-dry. Then, 150 μL of Tris pH 10.5 (10 mM) was added, and the absorbance was measured at 540 nm using a BMG LABTECH®- FLUOstar Omega microplate reader (Ortenberg, Germany). Half maximal inhibitory concentrations (IC$_{50}$) values were calculated for each experiment using GraphPad Prism 6 software. IC$_{50}$ values were reported as mean ±SD.

The inhibition was calculated using the following equation:

Inhibition %=100-Average Viability

The anticancer activity of 3-(2-(6-Methoxypyridin-3-yl)-4,5-diphenyl-1H-imidazol-1-yl)-N,N-dimethylpropan-1-amine was assessed against highly aggressive androgen-independent metastatic human prostate cancer cells (PC3) and osteosarcoma (MG-63) cells. These experiments showed that the present compound display excellent anti-proliferative activities against cancer cells (PC3) and osteosarcoma (MG-63) cells.

It is to be understood that the 3-(2-(6-Methoxypyridin-3-yl)-4,5-diphenyl-1H-imidazol-1-yl)-N,N-dimethylpropan-1-amine compound, compositions containing the same, and methods of using and producing the same are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A 3-(2-(6-Methoxypyridin-3-yl)-4,5-diphenyl-1H-imidazol-1-yl)-N,N-dimethylpropan-1-amine having the formula I:

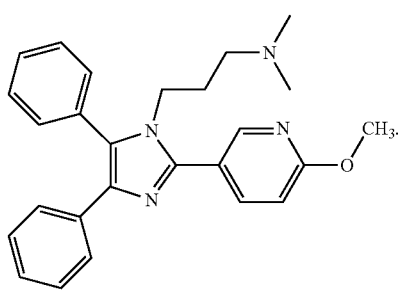

I

2. The 3-(2-(6-Methoxypyridin-3-yl)-4,5-diphenyl-1H-imidazol-1-yl)-N,N-dimethylpropan-1-amine compound of claim 1, wherein the compound is obtained as crystals.

3. The 3-(2-(6-Methoxypyridin-3-yl)-4,5-diphenyl-1H-imidazol-1-yl)-N,N-dimethylpropan-1-amine compound of claim 1, having a melting point of about 125° C. to about 127° C.

4. A pharmaceutically acceptable composition comprising a therapeutically effective amount of the 3-(2-(6-Methoxypyridin-3-yl)-4,5-diphenyl-1H-imidazol-1-yl)-N,N-dimethylpropan-1-amine compound of claim 1 and a pharmaceutically acceptable carrier.

5. A method of making the 3-(2-(6-Methoxypyridin-3-yl)-4,5-diphenyl-1H-imidazol-1-yl)-N,N-dimethylpropan-1-amine compound of claim 1, the method comprising:
adding benzil, 6-methoxy-3-pyridinecarboxaldehyde, ammonium acetate, and N,N-dimethyl-3-aminopropane to piperidinium hydrogen sulfate in an oil bath to obtain a reaction mixture;
heating the reaction mixture with stirring until reaction completion to obtain a crude product;
purifying the crude product by recrystallization using absolute ethyl alcohol; and
obtaining the 3-(2-(6-Methoxypyridin-3-yl)-4,5-diphenyl-1H-imidazol-1-yl)-N,N-dimethylpropan-1-amine compound.

6. The method of making the 3-(2-(6-Methoxypyridin-3-yl)-4,5-diphenyl-1H-imidazol-1-yl)-N,N-dimethylpropan-1-amine compound of claim 5, wherein the oil bath is at a temperature of about 20° C. to about 30° C.

7. The method of making the 3-(2-(6-Methoxypyridin-3-yl)-4,5-diphenyl-1H-imidazol-1-yl)-N,N-dimethylpropan-1-amine compound of claim 5, wherein heating is at a temperature of about 100° C.

8. The method of making the 3-(2-(6-Methoxypyridin-3-yl)-4,5-diphenyl-1H-imidazol-1-yl)-N,N-dimethylpropan-1-amine compound of claim 5, wherein after reaction completion the reaction mixture is washed with water.

9. The method of making the 3-(2-(6-Methoxypyridin-3-yl)-4,5-diphenyl-1H-imidazol-1-yl)-N,N-dimethylpropan-1-amine compound of claim 5, wherein the benzil, 6-methoxy-3-pyridinecarboxaldehyde, and ammonium acetate are added in an about 1:1:1 molar ratio.

10. The method of making the 3-(2-(6-Methoxypyridin-3-yl)-4,5-diphenyl-1H-imidazol-1-yl)-N,N-dimethylpropan-1-amine compound of claim 5, wherein the benzil, 6-methoxy-3-pyridinecarboxaldehyde, ammonium acetate, and N,N-dimethyl-3-aminopropane are added in an about 1:1:1:0.5 molar ratio.

11. The method of making the 3-(2-(6-Methoxypyridin-3-yl)-4,5-diphenyl-1H-imidazol-1-yl)-N,N-dimethylpropan-1-amine compound of claim 5, wherein the 3-(2-(6-Methoxypyridin-3-yl)-4,5-diphenyl-1H-imidazol-1-yl)-N,N-dimethylpropan-1-amine compound is obtained in an about 87% yield.

\* \* \* \* \*